United States Patent
Inada et al.

(10) Patent No.: US 7,271,291 B2
(45) Date of Patent: Sep. 18, 2007

(54) 1,3,5-TRIS (ARYLAMINO) BENZENES

(75) Inventors: Hiroshi Inada, Kobe (JP); Nobutaka Akashi, Kobe (JP); Tomoko Hayashi, Kobe (JP)

(73) Assignee: Bando Chemical Industries, Ltd., Kobe-shi (JP)

( * ) Notice: Subject to any disclaimer, the term of this patent is extended or adjusted under 35 U.S.C. 154(b) by 0 days.

(21) Appl. No.: 10/549,166

(22) PCT Filed: Mar. 15, 2004

(86) PCT No.: PCT/JP2004/003512

§ 371 (c)(1),
(2), (4) Date: Sep. 14, 2005

(87) PCT Pub. No.: WO2004/083161

PCT Pub. Date: Sep. 30, 2004

(65) Prior Publication Data

US 2006/0173216 A1 Aug. 3, 2006

(30) Foreign Application Priority Data

Mar. 18, 2003 (JP) ............... 2003-074646

(51) Int. Cl.
*C07C 211/54* (2006.01)
*H01L 35/24* (2006.01)
(52) U.S. Cl. .............. 564/336; 564/337; 257/40
(58) Field of Classification Search ........ 564/336, 564/337; 257/40
See application file for complete search history.

(56) References Cited

FOREIGN PATENT DOCUMENTS

CN 2002-111700 * 5/2002

OTHER PUBLICATIONS

CAPLUS abstract of Accession No. 2005:295951, Xu, Wei et al, "Composite cavity transport material," Chinese Application No. 2002-111700, published May 16, 2002.*

* cited by examiner

*Primary Examiner*—Kamal A. Saeed
*Assistant Examiner*—Janet L Coppins
(74) *Attorney, Agent, or Firm*—Hamre Schumann Mueller & Larson, P.C.

(57) ABSTRACT

The invention provides 1,3,5-tris(arylamino)benzenes represented by the general formula (I)

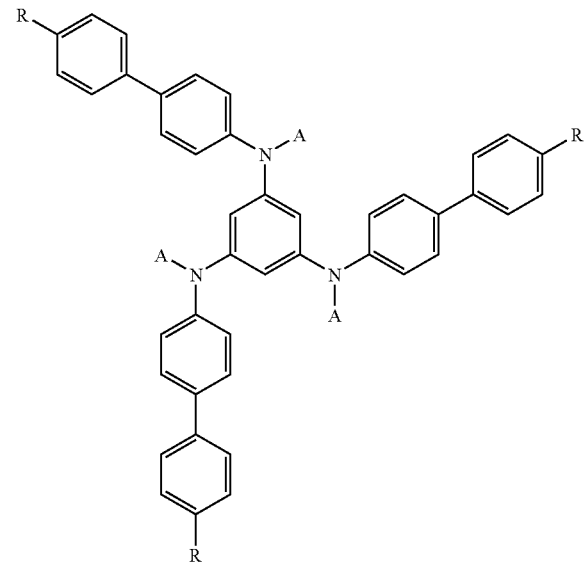

wherein A is naphthyl, anthryl or phenanthryl group, and R is hydrogen atom or diarylamino group.

These 1,3,5-tris(arylamino)benzenes have oxidation potentials in the range of about 0.5-0.6V, excellent reversibility in oxidation-reduction process, high glass transition temperatures and high heat resistance, so that they can form practicable organic semiconductor film readily by a coating method or a vacuum deposition method. In addition, they are capable of forming stable and durable amorphous film useful as high performance organic semiconductors at normal temperatures or higher with no aid of binder resins, that is, by themselves.

3 Claims, 6 Drawing Sheets

1,3,5-TRIS (ARYLAMINO) BENZENES

FIELD OF THE INVENTION

This invention relates to novel 1,3,5-tris(arylamino)-benzenes useful as organic semiconductors. More particularly, the invention relates to novel 1,3,5-tris(arylamino)benzenes that are superior in reversibility of oxidation-reduction process and can form stable organic semiconductor film readily by a coating method or a vacuum deposition method. Accordingly they are suitable for use as organic semiconductors in a variety of electronic devices such as hole transport agents in organic electroluminescence devices, electric charge transport agents in electrophotographic devices or organic semiconductors in solar batteries.

BACKGROUND ART

In recent years, organic semiconductors comprised of amorphous film of organic substances are in wide use in a variety of electronic devices. For example, an organic amorphous film is formed by preparing a coating composition comprised of a binder resin such as polycarbonate resin and a low molecular weight organic compound such as a triphenylamine derivative having photoelectric function dissolved in a suitable organic solvent and then by coating and drying the composition. The film thus formed is used as a positive hole transport layer in electrophotographic devices (JP-A-1999-174707). Similarly, an organic amorphous film is formed by preparing a coating composition comprised of a so-called star-burst compound dissolved in a suitable organic solvent and then by coating and drying the composition. The film thus formed is used as an organic p-type semiconductor film in solar batteries (JP-A-2000-174657).

BACKGROUND ART

As described above, organic semiconductor films comprised of organic amorphous film have been prepared by preparing a coating composition using a low molecular weight organic compound having photoelectric function together with a binder resin and then coating the composition on a suitable substrate and drying the composition. However, many of the low molecular weight organic compounds that have hitherto been known have low oxidation potentials, and accordingly when they are formed to organic semiconductor films by a coating method, they are easily oxidized, so that it is not easy to form a film using such low molecular weight organic compounds. They have also no sufficient reversibility in oxidation-reduction process so that it is difficult to prepare organic semiconductor film durable and suitable for practical use. In addition, the resulting organic semiconductor films have no sufficient heat resistance and hence the electronic devices using such organic semiconductor films are inferior in stability and durability.

As typical low molecular weight organic compounds that have photoelectric function and are usable for preparing organic semiconductor films, there have been known such compounds as N,N,N',N'-tetramethylbenzidine, N,N,N',N'-tetraphenyl-(1,1'-biphenyl)-4,4'-diamine, N,N'-diethyl-N,N'-diphenyl-(1,1'-biphenyl)-4,4'-diamine, or N,N,N',N'-tetra(3-methylphenyl)-4,4'-diaminostilbene. However, these low molecular weight organic compounds form only amorphous films that are by themselves not so stable as to be used as electric charge transport agents in organic photosensitive elements. Accordingly, they are dispersed in a binder resin (that is, diluted with a binder resin), and the resulting dispersion is applied to a substrate to form an amorphous film.

Thus, the known low molecular weight organic compounds that form an organic amorphous film are diluted with a binder resin and are influenced by the binder resin which forms a matrix for the amorphous film so that the organic amorphous film cannot exhibit sufficiently the properties that they originally possess. In addition, if the known low molecular weight organic compounds form an amorphous film that is relatively stable at normal temperatures with the aid of a binder, they have low glass transition temperatures so that the film is poor in heat resistance and is not suitable for practical use.

Accordingly, the development of low molecular weight organic compounds that have photoelectric conversion function and are capable of forming amorphous film by themselves at normal temperatures or higher has been pushed on with in recent years, and as results, some nitrogen-containing polynuclear aromatic compounds called star-burst molecules have been proposed as such low molecular weight organic compounds.

The star-burst molecules are divided into three groups based on their molecular structures: compounds having triphenylamine structure (triphenylamines), compounds having triaminobenzene structure (triaminobenzenes) and compounds having triphenylbenzene structure (triphenylbenzenes). Beside the above-mentioned, compounds having triphenylmethane structure are also proposed.

The triphenylamines include, for example, 4,4',4"-tris-(N,N-diphenylamino)triphenylamine (TDATA) (1) having the structure (1)

as described in JP-A-1990-224353; 4,4',4"-tris(N-phenyl-N-m-tolylamino)triphenylamine (m-MTDATA) (2) having the structure (2)

as described in JP-A-1990-224353; 4,4',4"-tris(N-(2-naphthyl)-N-phenylamino)triphenylamine (2-TNATA) (3) having the structure (3)

as described in JP-A-1996-291115; and 4,4',4"-tris(N-(1-naphthyl)-N-phenylamino)triphenylamine (1-TNATA).

These triphenylamines are reversible in oxidation-reduction process, however, they have low oxidation potentials (oxidation potential against Ag/Ag$^+$ electrode, the same hereunder) of about 0.1V or less so that there is a problem in that they are easily oxidized when they are formed to organic semiconductor film by a coating method.

m-MTDATA has a glass transition temperature of about 77° C. so that it is difficult to use the compound in practical electronic devices, and on the other hand, 2- or 1-TNATA has a glass transition temperature of about 110° C. and is capable of forming heat-resistant organic amorphous film, but the compound is readily crystallized so that the resulting organic amorphous film is lacking in stability or durability.

The triphenylbenzenes include, for example, 1,3,5-tris(4-(N,N-diphenylaminophenyl)benzene (TDAPB) having the structure (4)

(4)

and 1,3,5-tris(4-(N-tolyl-N-phenylaminophenyl)benzene (MTDAPB) (5) having the structure

(5)

as described in Bando Technical Report, Vol. 2, pp. 9-18, 1998 (Bando Chemical Industries, Ltd.).

The triphenylbenzenes are capable of forming amorphous film and have oxidation potentials in the range of 0.6-0.7V, but they are irreversible in oxidation-reduction process so that they are not suitable for use in practical use as organic semiconductors.

In turn, the triaminobenzenes include, for example, 1,3,5-tris(N-methylphenyl-N-phenylamino)benzene (MTDAB) having the structure (6)

(II)

as described in Bando Technical Report, Vol. 2, pp. 9-18, 1998 (Bando Chemical Industries, Ltd.).

The triaminobenzenes also have oxidation potentials in the range of 0.5-0.6V, but they are irreversible in oxidation-reduction process, like the above-mentioned triphenylbenzenes, and in addition, they have glass transition temperatures as low as about 60° C. or less so that they are not suitable for use in practical use as organic semiconductors. They have further problems in heat resistance.

The invention has been accomplished to solve the above-mentioned problems in the star-burst molecules having triaminobenzene structure for use as materials for organic semiconductors.

Accordingly, it is an object of the invention to provide novel 1,3,5-tris(arylamino)benzenes that have oxidation potentials in the range of about 0.5-0.6V and high glass transition temperatures and that are superior in reversibility in oxidation-reduction process and heat resistance so that they are readily formed to organic semiconductor film by a coating method or vacuum deposition method, as well as they are capable of forming stable and durable high-performance organic semiconductor film by themselves because they are capable of forming amorphous film by themselves with no aid of binder resins at normal temperatures or higher.

SUMMARY OF THE INVENTION

The invention provides 1,3,5-tris(arylamino)benzenes represented by the general formula (I)

wherein A is naphthyl, anthryl or phenanthryl group, and R is hydrogen atom or diaryl amino group.

BEST MODE FOR CARRYING OUT THE INVENTION

The 1,3,5-tris(arylamino)benzenes of the invention are expressed by the general formula (I)

(I)

(I)

wherein A is naphthyl, anthryl or phenanthryl group, and preferably 1-naphthyl, 2-naphthyl, 9-anthryl or 9-phenanthryl. R is hydrogen atom or diarylamino group. As the diaryl amino groups, there are mentioned, for example, those in which the aryl group is independently phenyl, tolyl or naphthyl group. Accordingly, the diarylamino group is exemplified by, for example, diphenylamino, phenyltolylamino (in which the tolyl is preferably o-tolyl or m-tolyl), phenylnaphthylamino (in which the naphthyl is 1- or 2-naphthyl), and so on. Among those exemplified, asymmetric diarylamino groups such as phenyltolylamino or phenylnaphthylamino group are preferred.

The 1,3,5-tris(arylamino)benzenes of the invention is obtained by the reaction of 1,3,5-tris(1-naphthylamino)benzenes represented by the general formula (II)

(II)

wherein R is the same as the above with an aryl halide represented by the general formula (III)

A—X (III)

wherein A is the same as above and X is a halogen atom, depending on the 1,3,5-tris(arylamino)benzene to be obtained, in the presence of a base and copper powder under an atmosphere of inert gas such as nitrogen, argon or helium using a crown compound such as 18-crown-6 (or 1,4,7,10, 13,16-hexaoxacyclooctadecane) as a catalyst, if necessary, in a solvent.

The aryl halides preferably used are, for example, iodides or bromides. If necessary, chlorides are also used. By way of example, when 1,3,5-tris(N-(4-biphenylyl)-N-(1-naphthyl)-amino)benzene (TBNAB) is to be obtained, 4-iodobiphenyl is preferably used as the aryl halide, and on the other hand, when 1,3,5-tris(N-4-(4'-phenyl-N-m-tolylamino)biphenylyl)-N-(1-naphthyl)amino)benzene (m-MDPABNAB) is to be obtained, 4'-iodobiphenyl-4-yl)phenyl-m-tolylamine is preferably used as the aryl halide.

The aryl halides are used in excess in relation to 1,3,5-tris(4-biphenylylamino)benzene. More particularly, the aryl halides are used preferably in an amount of more than three mole parts, more preferably in an amount of 3-10 mole parts, and most preferably in an amount of 3.5-5 mole parts, in relation to mole part of 1,3,5-tris(4-biphenylylamino)benzene.

The bases used in the reaction include, for example, hydroxides of alkali metals such as potassium hydroxide, or carbonates or hydrogen carbonates of alkali metals, especially those of sodium or potassium, and in particular, potassium carbonate is preferred. In the reaction, any solvent may be used so far as it does not inhibit the reaction, and usually hydrocarbon solvents such as decalin, mesitylene or heptane are preferably used. The reaction temperature is not specifically limited, but it is usually in the range of 140-190° C., and the reaction time is usually in the range of 5-30 hours.

After the completion of reaction, the reaction product is dissolved in an organic solvent and the catalyst used is separated by filtration, and then the reaction product is separated and purified by column chromatography using an appropriate eluate to provide a high purity product in high yields.

The 1,3,5-tris(arylamino)benzenes of the invention have oxidation potentials in the range of about 0.5-0.6V. From the structural point of view, in the first place, they have a skeleton of triphenylamines in which one of the substituents on each of the nitrogen atoms is biphenylyl group, so that the biphenylyl substituent covers the active cite of the compound thereby securing the reversibility in oxidation-reduction process. In the second place, said each of the nitrogen atoms carries naphthyl, anthryl or phenanthryl group thereon as a substituent so that the compound has high glass transition temperatures and hence high heat resistance, and in addition, the compound has improved reversibility in oxidation-reduction reaction.

As described above, the 1,3,5-tris(arylamino)benzenes of the invention are suitably used for preparation of organic semiconductor film by a coating method or a vacuum deposition method that is superior in stability and heat resistance. Furthermore, the 1,3,5-tris(arylamino)benzenes of the invention are capable of forming amorphous film by themselves at normal temperatures or higher, and hence they are capable of forming high-performance durable organic semiconductor film by themselves.

Accordingly, the 1,3,5-tris(arylamino)benzenes of the invention are suitably used as elements in various electronic devices such as hole transport agents in electroluminescence devices, charge transport agents in electrophotography or organic semiconductors in solar batteries, although they are not specifically limited in their use.

EXAMPLE

The invention is described in more detail with reference to examples, however, the invention is not limited thereto.

Example 1

Preparation of 1,3,5-tris(1-naphthylamino)benzene 4.4 g of phloroglucinol, 25 g of 1-naphthlamine and 0.5 g of iodine were placed in a 100 mL capacity three necked flask and the reaction was carried out at a temperature of 140° C. for 4 hours with stirring under a nitrogen atmosphere. After the reaction, the resultant reaction mixture was washed with methanol, hexane and methanol in this order, followed by drying to provide the desired 1,3,5-tris(1-naphthylamino)benzene as slightly reddish solid. The yield was 25%.

Preparation of 1,3,5-tris(N-(4-biphenylyl)-N-(1-naphthyl)amino)-benzene (TBNAB)

2.0 g of 1,3,5-tris(1-naphthylamino)benzene, 5.0 g of 4-iodobiphenyl, 3.7 g of potassium carbonate, 2 g of copper powder, 0.3 g of 18-crown-6 (or 1,4,7,10,13,16-hexaoxacyclooctadecane) and 10 mL of mesitylene as a reaction solvent were placed in a 100 mL capacity glass flask and the reaction was carried out at a temperature of 170° C. for 17 hours under a nitrogen atmosphere. After the reaction, the resultant reaction mixture was extracted with toluene and the toluene solution was subjected to silica gel chromatography to fractionate the reaction product. The reaction product was then purified by recrystallization from a mixed solvent of toluene/hexane and then by sublimation to provide 1.2 g of the desired 1,3,5-tris(N-(4-biphenylyl)-N-(1-naphthyl)amino)benzene (TBNAB). The yield was 32%.

Elemental Analysis (%):

|  | C | H | N |
|---|---|---|---|
| Calculated: | 90.25 | 5.36 | 4.39 |
| Measured: | 89.96 | 5.44 | 4.32 |
| Mass analysis: M+ = 957 | | | |

Figure 1:
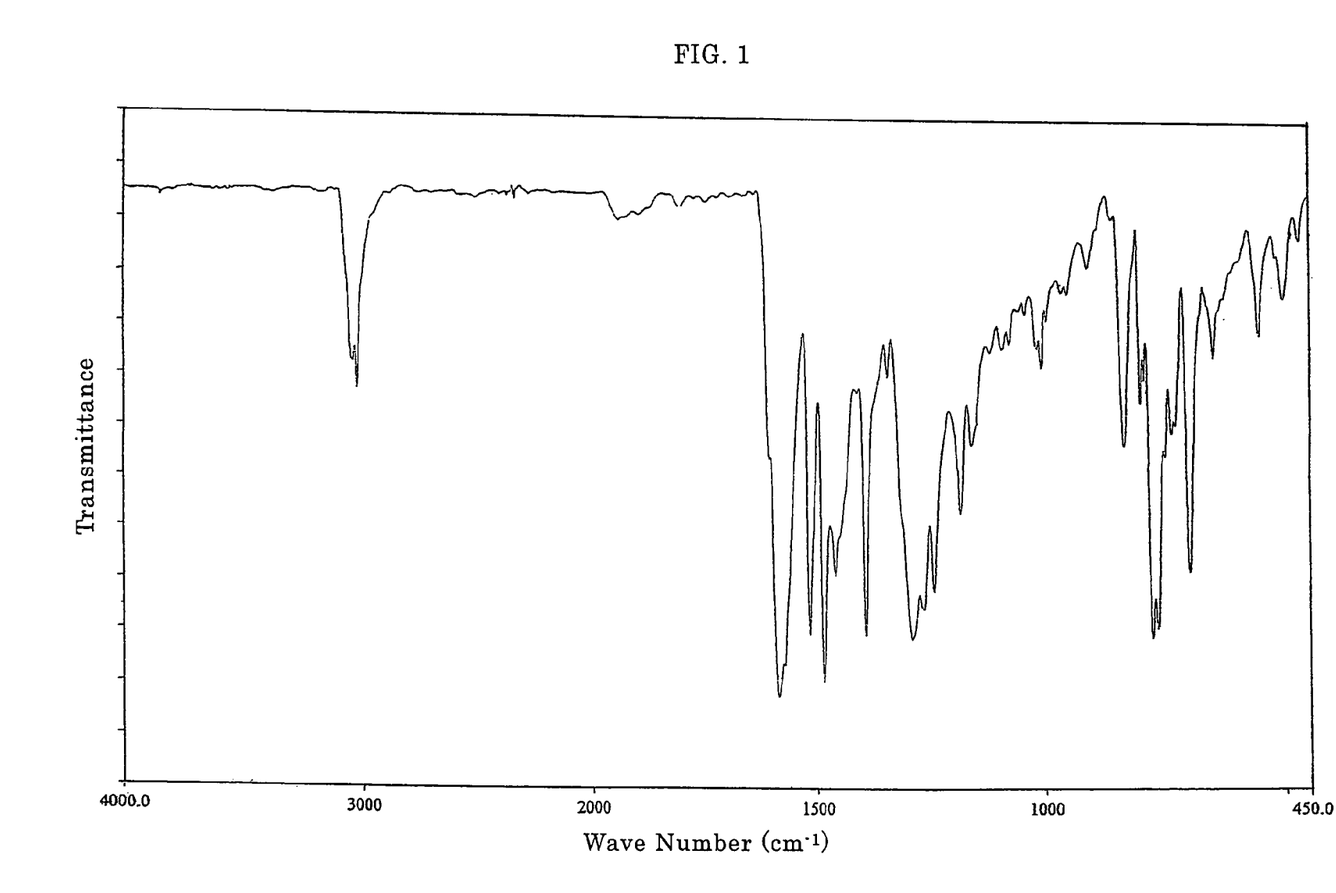
FIG. 1 is an infrared absorption spectrum of 1,3,5-tris-(N-(4-biphenylyl)-N-(1-naphthyl)amino)benzene (TBNAB) of the invention.

Infrared absorption spectrum is shown in FIG. 1.

Figure 2:
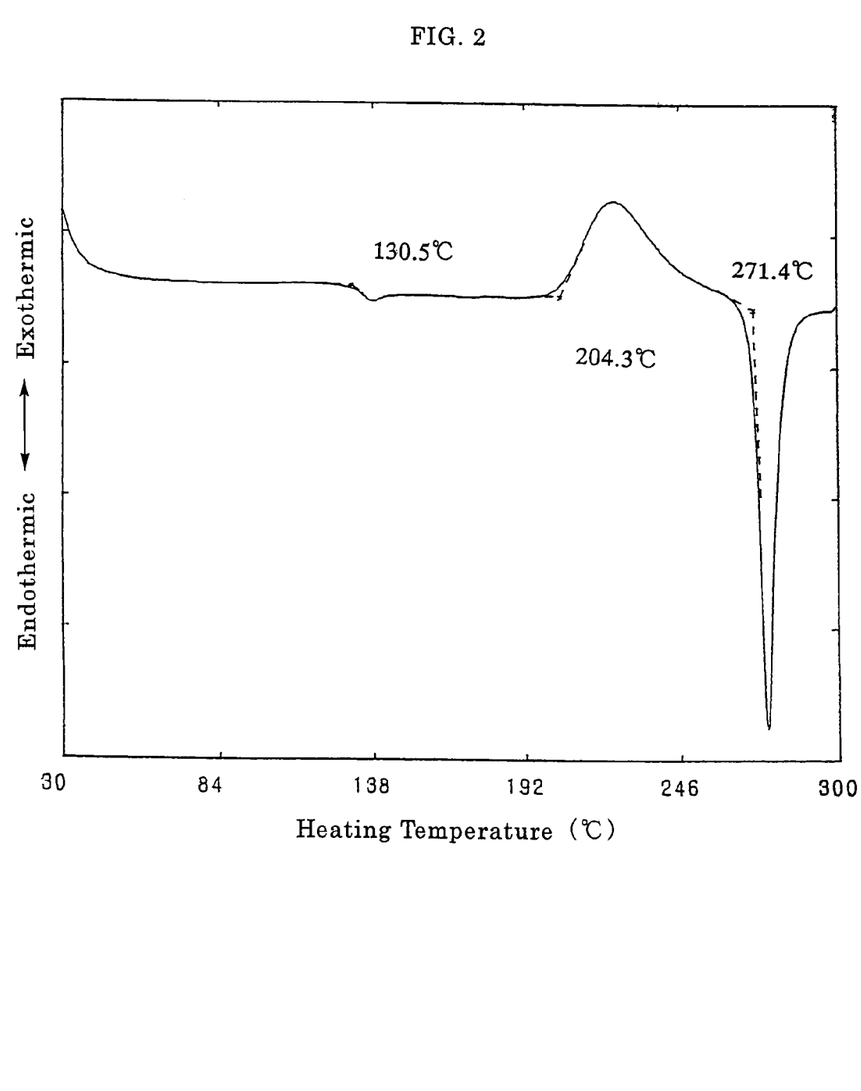
FIG. 2 is a differential scanning calorimetry (DSC) curve of 1,3,5-tris-(N-(4-biphenylyl)-N-(1-naphthyl)amino)benzene (TBNAB) of the invention.

Differential Scanning Calorimetry (DSC):

About 5 mg of TBNAB was weighed as a sample, and it was melted in a differential scanning calorimetric device and cooled to room temperature at a rate of 50° C. per minute. The sample did not crystallized, but it became amorphous glass. Subsequently, the thermal characteristics of the sample were measured by heating at a rate of 5° C. per minute by using an aluminum plate as a reference. As the DSC chart is shown in FIG. 2, the compound was found to have a glass transition temperature (Tg) of 130° C., a crystallization temperature (Tc) of 204° C. and a melting point (Tm) of 271° C.

Figure 3:
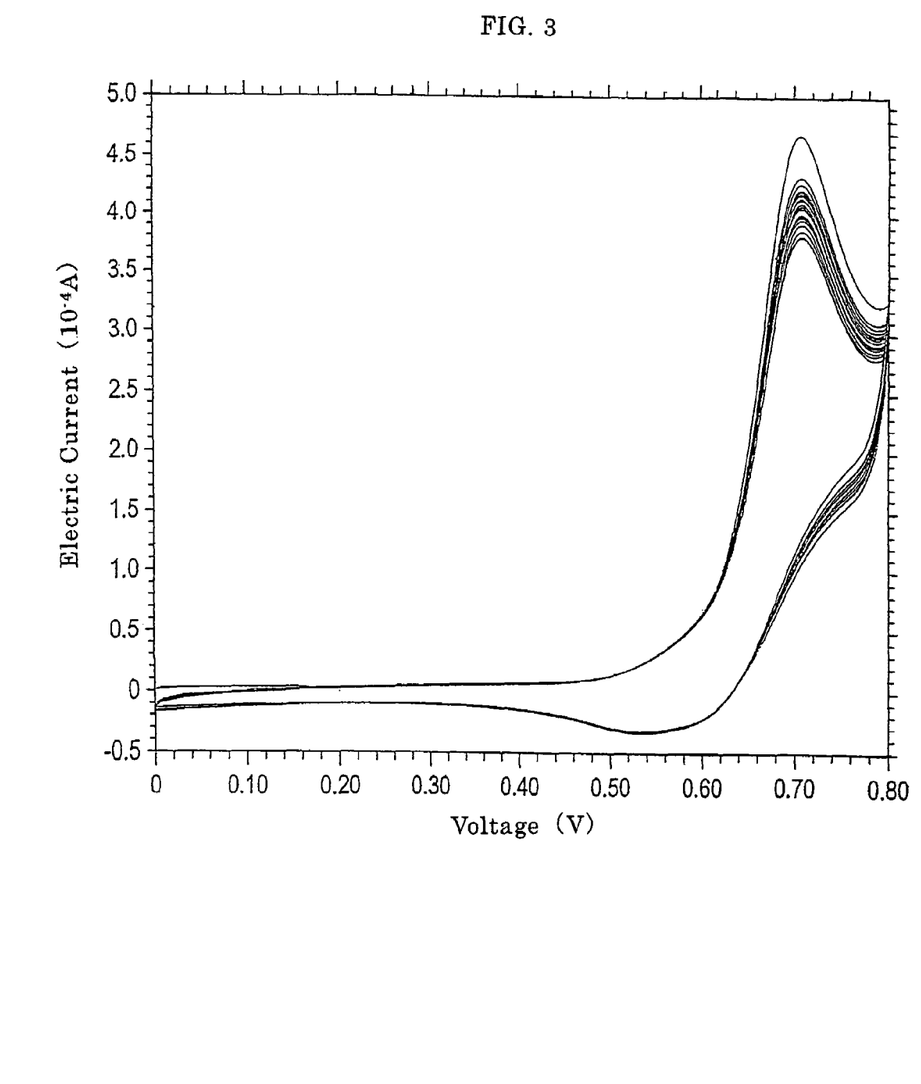
FIG. 3 is a cyclic voltamogram of 1,3,5-tris-(N-(4-biphenylyl)-N-(1-naphthyl)amino)benzene (TBNAB) of the invention.

Cyclic Voltammetry (CV):

TBNAB was dissolved in dichloromethane and the solution was arranged at a concentration of $10^{-3}$ M. The oxidation reduction characteristics of the sample were measured using tetrabutylammonium perchlorate (($n$-$C_4H_9$)$_4$NClO$_4$ (0.1M)) as a supporting electrolyte and Ag/Ag$^+$ as a reference electrode at a scan speed of 50 mV/s. As the CV chart is shown in FIG. 3, the compound has an oxidation potential of 0.62V (vs. Ag/Ag$^+$). It was found that the compound had reversibility in oxidation reduction process after 50 times measurements, indicating that the compound is suitably used as organic positive hole transport agents.

Example 2

Preparation of 1,3,5-tris(N-4-(4'-N-phenyl-N-m-tolylamino)-biphenylyl-N-(1-naphthyl)amino)benzene)(m-MDPABNAB)

1.1 g of 1,3,5-tris(1-naphthylamino)benzene, 5 g of (4'-iodobiphenyl-4-yl)phenyl-m-tolylamine, 3 g of potassium carbonate, 250 mg of copper powder, 290 mg of 18-crown-6 (or 1,4,7,10,13,16-hexaoxacyclooctadecane) and 15 mL of solvent, mesitylene, were placed in a 100 mL capacity flask and the reaction was carried out at a temperature of 160° C. for 21 hours under a nitrogen atmosphere. After the reaction, the resultant reaction mixture was extracted with toluene and the toluene solution was subjected to silica gel chromatography to fractionate the reaction product. The reaction product was then purified by recrystallization and dried, and then by sublimation to provide 1.4 g of the desired 1,3,5-tris(N-4-(4'-N-phenyl-N-m-tolylamino)-biphenyl)-N-(1-naphthyl)amino)benzene (m-MDPABNAB). The yield was 42%.

Elemental Analysis (%):

|  | C | H | N |
|---|---|---|---|
| Calculated: | 88.77 | 5.64 | 5.60 |
| Measured: | 88.72 | 5.67 | 5.55 |
| Mass analysis: M+ = 1501 | | | |

Figure 4:
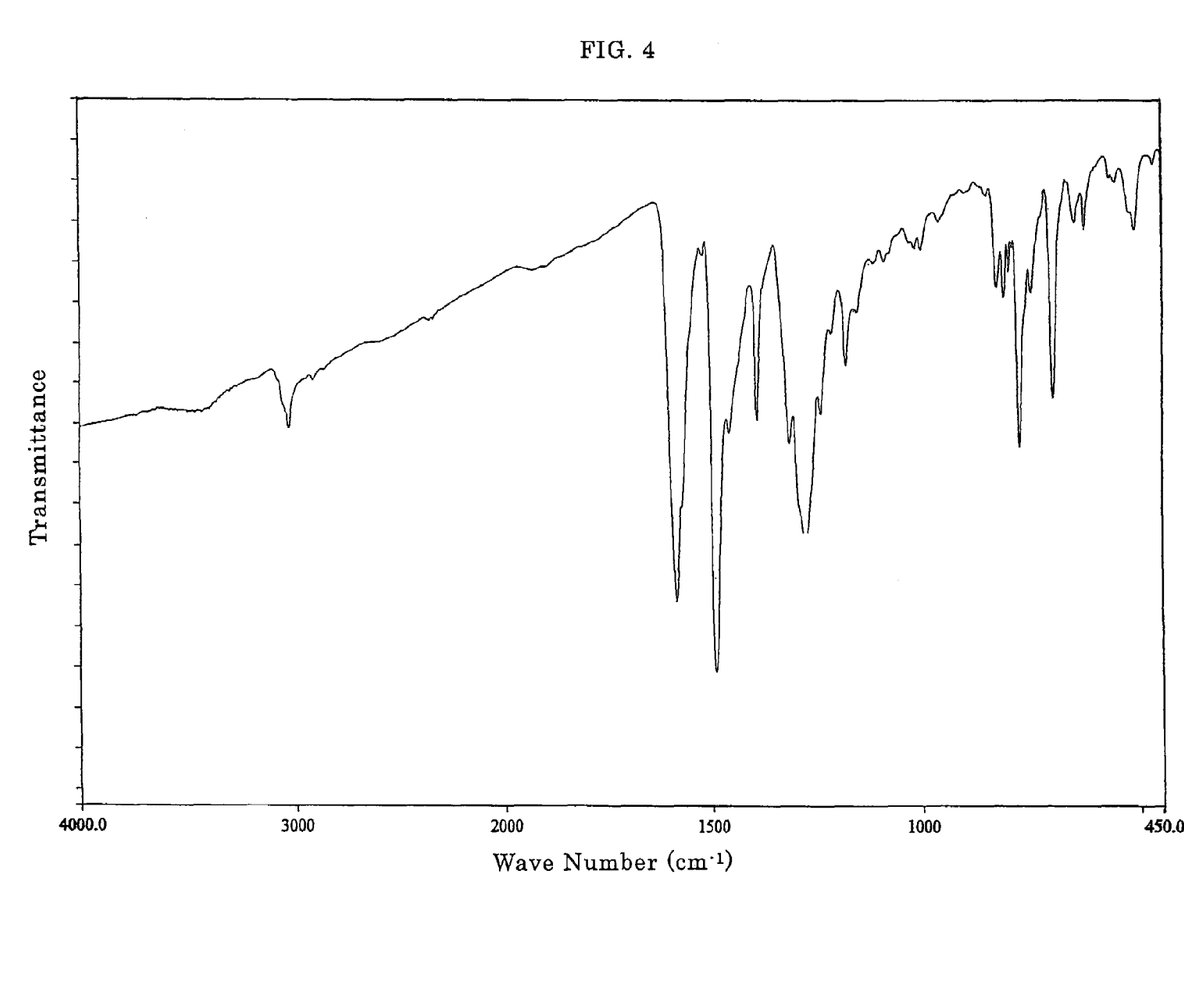
FIG. 4 is an infrared absorption spectrum of 1,3,5-tris(N-4-(4'-N-phenyl-N-m-tolylamino)biphenylyl-N-(1-naphthyl)-amino)benzene (m-MDPABNAB) of the invention.

Infrared absorption spectrum is shown in FIG. 4.

Figure 5:
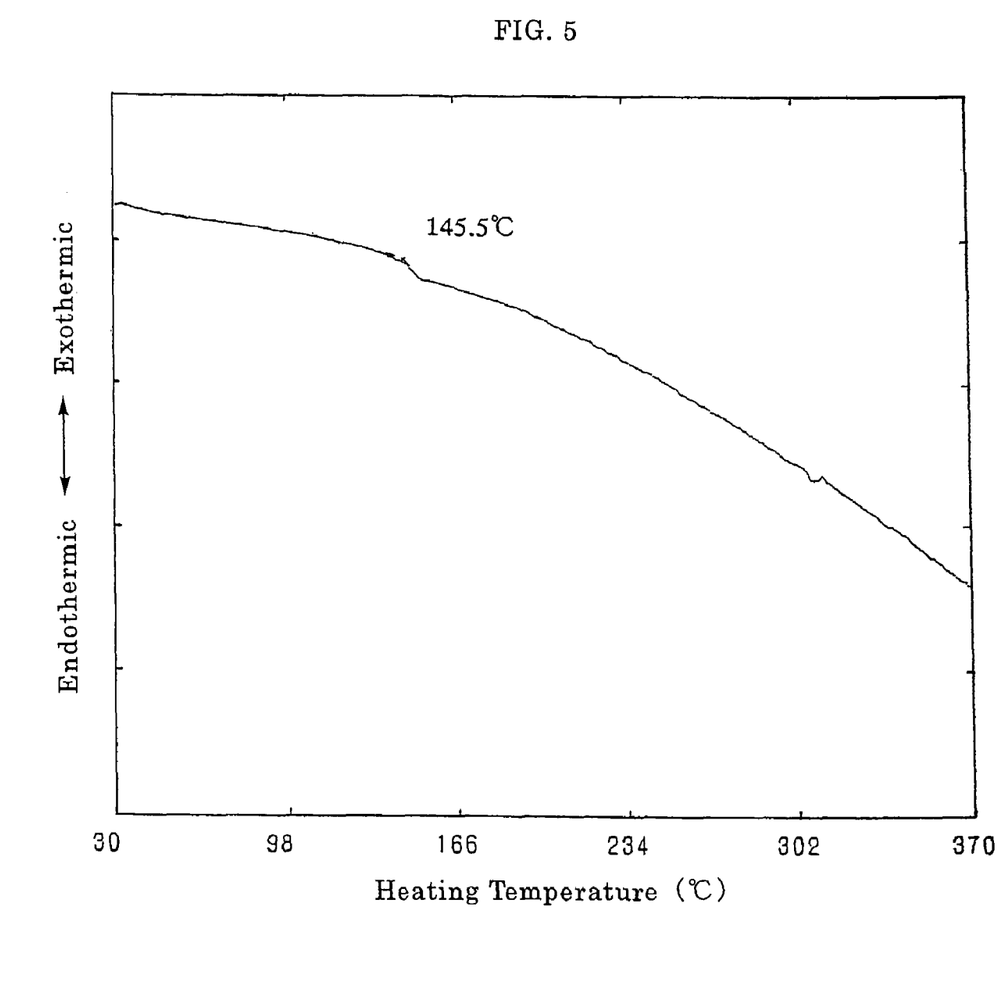
FIG. 5 is a differential scanning calorimetry (DSC) curve of 1,3,5-tris(N-4-(4'-N-phenyl-N-m-tolylamino)biphenylyl-N-(1-naphthyl)amino)benzene (m-MDPABNAB) of the invention.

Differential Scanning Calorimetry (DSC):

About 5 mg of m-MDPABNAB was weighed as a sample, and it was melted in a differential scanning calorimetric device and cooled to room temperature at a rate of 50° C. per minute. The sample did not crystallized, but it became amorphous glass. Subsequently, the thermal characteristics of the sample were measured by heating at a rate of 5° C. per minute by using an aluminum plate as a reference. As the DSC chart is shown in FIG. 5, the compound has a glass transition temperature (Tg) of 145° C., but neither crystallization temperature (Tc) nor melting point (Tm) was not observed.

Figure 6:
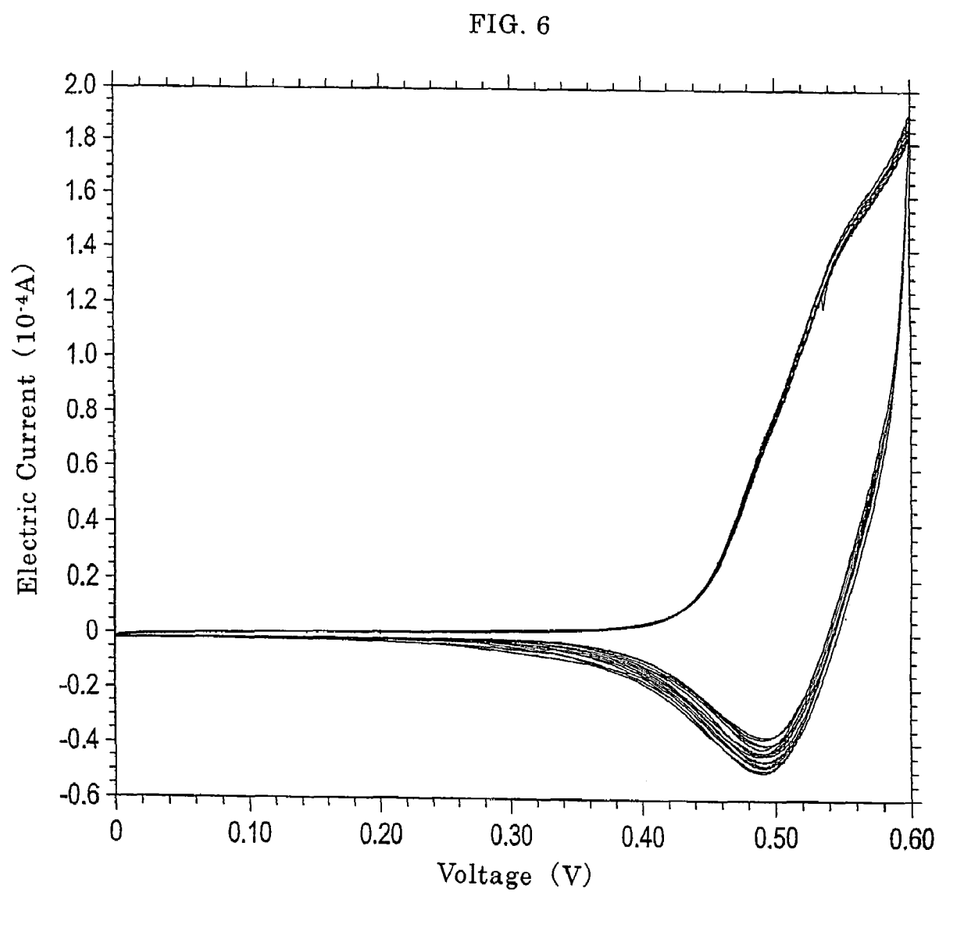
FIG. 6 is a cyclic voltamogram of 1,3,5-tris(N-4-(4'-N-phenyl-N-m-tolylamino)biphenylyl-N-(1-naphthyl)amino) benzene (m-MDPABNAB) of the invention.

Cyclic Voltammetry (CV):

m-MDPABNAB was dissolved in dichloromethane and the solution was arranged at a concentration of $10^{-3}$M. The oxidation reduction characteristics of the sample were measured using tetrabutylammonium perchlorate (($n$-$C_4H_9$)$_4$NClO$_4$ (0.1M)) as a supporting electrolyte and Ag/Ag$^+$ as a reference electrode at a scan speed of 10 mV/s. As the CV chart is shown in FIG. 6, the compound has an oxidation potential of 0.52V (vs. Ag/Ag$^+$). It was found that the compound had reversibility in oxidation reduction process after 50 times measurements, indicating that the compound is suitably used as organic positive hole transport agents.

INDUSTRIAL APPLICABILITY OF THE INVENTION

The invention provides novel 1,3,5-tris(arylamino)-benzenes. They have oxidation potentials in the range of about 0.5-0.6V and an excellent reversibility in oxidation-reduction process, as well as high glass transition temperatures and excellent heat resistance, and hence they readily form amorphous film useful as organic semiconductors or hole transport agents by a coating method or a vacuum deposition method. In addition, the 1,3,5-tris(arylamino)benzenes of the invention are capable of forming amorphous film by themselves at normal temperatures or higher so that they find wide applications as organic amorphous materials in a variety of fields.

The invention claimed is:

1. A 1,3,5-tris(arylamino)benzene represented by the general formula (I)

wherein A is naphthyl, anthryl or phenanthryl group, and R is hydrogen atom or diarylamino group.

2. 1,3,5-tris(N-(4-biphenylyl)-N-(1-naphthyl)amino)benzene.

3. 1,3,5-tris(N-4-(4'-N-phenyl-N-m-tolylamino)biphenylyl-N-(1-naphthyl)amino)benzene.

* * * * *